United States Patent
Yoshida et al.

(10) Patent No.: US 7,431,753 B2
(45) Date of Patent: Oct. 7, 2008

(54) OXYGEN ENRICHMENT APPARATUS

(75) Inventors: Toshiyuki Yoshida, Shiga (JP); Yasuo Oushima, Shiga (JP); Kazuhisa Morishita, Shiga (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 402 days.

(21) Appl. No.: 11/033,312

(22) Filed: Jan. 12, 2005

(65) Prior Publication Data

US 2005/0161044 A1    Jul. 28, 2005

(30) Foreign Application Priority Data

Jan. 13, 2004    (JP)    ............... 2004-005250

(51) Int. Cl.
*B01D 53/22* (2006.01)
*A62B 7/00* (2006.01)

(52) U.S. Cl. .................. 96/4; 96/7; 96/11; 96/417; 95/54; 55/357; 55/467; 55/473; 128/204.18; 128/204.22; 128/205.11; 128/205.27

(58) Field of Classification Search ............ 96/4, 96/8, 10, 11, 115, 121, 123, 143, 381, 382, 96/7, 417; 95/54; 55/467, 471, 473, 357; 128/200.24, 204.18, 204.21, 204.22, 205.11, 128/205.27, 206.27
See application file for complete search history.

(56) References Cited

U.S. PATENT DOCUMENTS

| | | | | |
|---|---|---|---|---|
| 3,369,343 A | * | 2/1968 | Robb | ................ 96/4 |
| 3,850,598 A | * | 11/1974 | Boehm | ................ 96/146 |
| 4,789,388 A | * | 12/1988 | Nishibata et al. | ................ 96/7 |
| 4,826,510 A | * | 5/1989 | McCombs | ............. 128/205.11 |
| 4,971,609 A | * | 11/1990 | Pawlos | ................ 96/128 |
| 5,144,945 A | | 9/1992 | Nishino et al. | |
| 5,428,868 A | * | 7/1995 | Safdeye et al. | ............. 16/113.1 |
| 5,902,379 A | * | 5/1999 | Phillips et al. | ................ 96/4 |
| 6,126,721 A | * | 10/2000 | Nemser et al. | ................ 95/54 |
| 6,520,176 B1 | * | 2/2003 | Dubois et al. | ........... 128/200.24 |
| 6,651,658 B1 | | 11/2003 | Hill et al. | |
| 7,135,059 B2 | * | 11/2006 | Deane et al. | ................ 96/153 |
| 7,166,148 B2 | * | 1/2007 | Lyons et al. | ................ 95/54 |
| 7,273,051 B2 | * | 9/2007 | Whitley et al. | ............. 128/205.11 |
| 2002/0096174 A1 | * | 7/2002 | Hill et al. | ............. 128/205.11 |

FOREIGN PATENT DOCUMENTS

| | | |
|---|---|---|
| EP | 0324056 | 7/1989 |
| JP | 04-314457 | 11/1992 |
| JP | 3096113 | 9/2003 |

* cited by examiner

*Primary Examiner*—Jason M Greene
(74) *Attorney, Agent, or Firm*—Bacon & Thomas, PLLC

(57) ABSTRACT

An oxygen enrichment apparatus includes a main body including an oxygen enriching unit and a pump unit for supplying oxygen-enriched air obtained by the oxygen enriching unit to a predetermined place; a ventilating unit for suctioning exterior air into the main body and discharging the exterior air out of the main body after supplying the exterior air into the oxygen enriching unit; and a control unit for controlling the pump unit and the ventilating unit. The ventilating unit and the control unit are installed in the main body. The main body further includes therein a secondary battery serving as a power supply for supplying a power to the pump unit, the ventilating unit and the control unit.

10 Claims, 12 Drawing Sheets

OXYGEN ENRICHMENT APPARATUS

FIELD OF THE INVENTION

The present invention relates to an oxygen enrichment apparatus capable of providing a user with oxygen-enriched air.

BACKGROUND OF THE INVENTION

Figure 12:
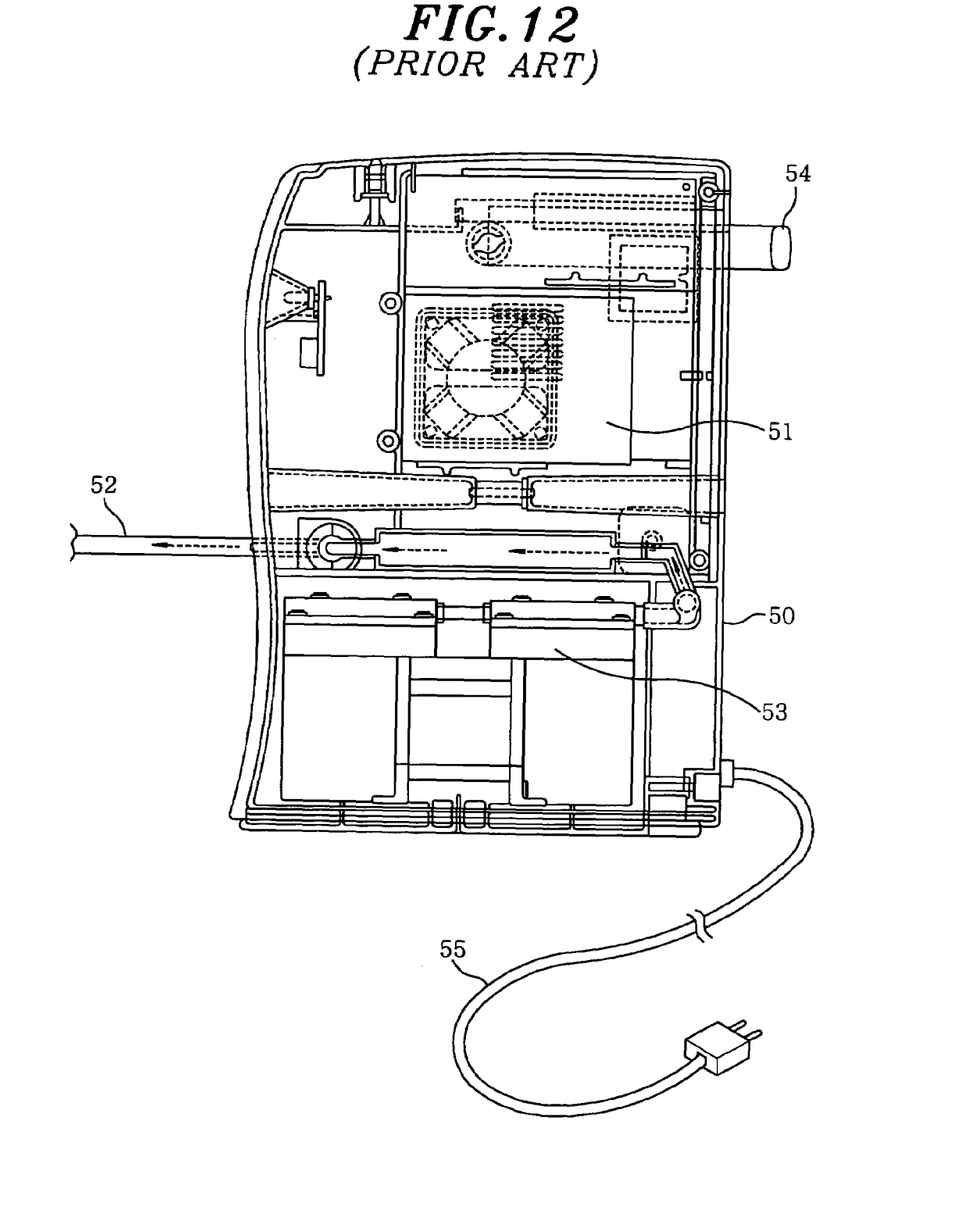
FIG. 12 is a cross sectional view of a conventional oxygen enrichment apparatus.

A conventional oxygen enrichment apparatus will be described with reference to FIG. 12, which provides a cross sectional view thereof. Main body 50 of the oxygen enrichment apparatus incorporates therein oxygen enriching unit 51 for increasing an oxygen concentration in the air and pump unit 53 for supplying discharge unit 52 with oxygen-enriched air obtained by oxygen enriching unit 51. Further, handle 54 for allowing a user to carry the apparatus and power cord 55 for supplying a power to pump unit 53 are also installed in main body 50. Discharge unit 52 is configured to communicate with a discharge port (not shown) provided in a headset (not shown) which is to be worn by the user on the head.

If the user wears the headset on his/her head, plugs power cord 55 in an indoor wall socket and turns on a power switch (not shown) of main body 50, the operation of pump unit 53 is initiated, whereby exterior air is suctioned into oxygen enriching unit 51 and oxygen-enriched air obtained thereby is sent to discharge unit 52, allowing the user to inhale the oxygen enriched air through the discharge port located near the user's mouth (see, for example, Japanese Utility Model No. 3096113).

Since, however, main body 50 in the conventional oxygen enrichment apparatus is operated by using an AC power, the use of the apparatus is limited only to an indoor place. That is, the apparatus could not be used outdoors or in a car where a commercial power source is not provided.

Recently, as the oxygen enrichment apparatus is gaining popularity, there is an increased demand for use for various purposes in various places: for example, use during an exercise or studying and use in an automobile. Thus, the above-mentioned spatial limitation in using the oxygen enrichment apparatus has been a problem to be solved.

SUMMARY OF THE INVENTION

It is, therefore, an object of the present invention to provide an oxygen enrichment apparatus capable of being used outdoors or in a vehicle such as an automobile or a train where a commercial power source is not provided, while improving the reliability of electric components incorporated therein.

In accordance with a preferred embodiment of the present invention, there is provided an oxygen enrichment apparatus including: a main body including an oxygen enriching unit and a pump unit for supplying oxygen-enriched air obtained by the oxygen enriching unit to a predetermined place; a ventilating unit for suctioning exterior air into the main body and discharging the exterior air out of the main body after supplying the exterior air into the oxygen enriching unit; and a control unit for controlling the pump unit and the ventilating unit, wherein the ventilating unit and the control unit are installed in the main body, and the main body further includes therein a secondary battery serving as a power supply for supplying a power to the pump unit, the ventilating unit and the control unit. Since the oxygen enrichment apparatus of the present invention includes the secondary battery, it can be used outdoors and at inside of a vehicle where there is no AC power source available, thereby increasing the usability thereof.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

Hereinafter, preferred embodiments of the present invention will be described with reference to the accompanying drawings. It should be noted that the preferred embodiments are only for illustration purpose and the scope of the present invention is not limited thereto.

An oxygen enrichment apparatus in accordance with a preferred embodiment of the present invention will now be described in conjunction with FIGS. 1 to 11.

Reference numeral 1 is for a box-shaped main body constructed vertically long by joining front and back case 1a and 1b together with each other, which are fixed to bottom plate 2 by using screws. Reference numeral 3 is for an inner case provided in main body 1, which is formed by joining left and right case 3a and 3b together with each other. The inner case is detachably fixed to bottom plate 2 of main body 1 by using screws. Reference numeral 4 represents a top plate for covering a top opening of main body 1, wherein top plate 4 is detachably installed at main body 1.

Reference numeral 5 is for a pump unit including, e.g., a bellows pump installed in a lower portion of inner case 3. Pump unit 5 is configured to communicate with oxygen enriching unit 15 to be described later and is elastically installed to bottom plate 2 as follows.

Figure 7A:
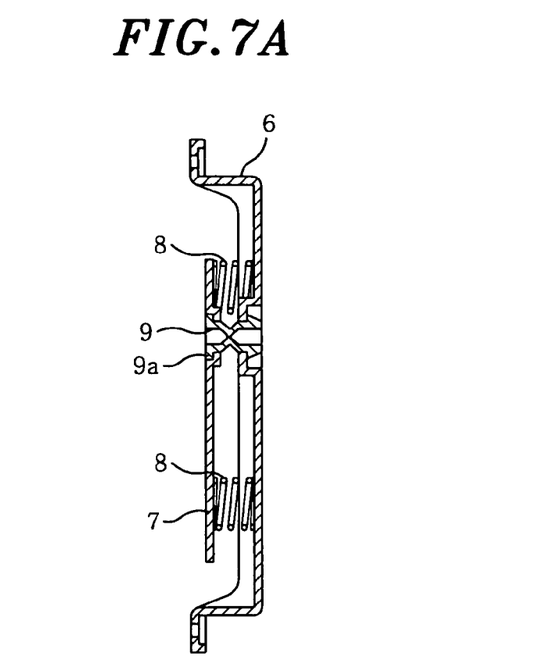
FIGS. 7A and 7B offer a cross sectional view and a plan view showing an assembled state of a base plate and an attachment plate of the oxygen enrichment apparatus, respectively.
Figure 7B:
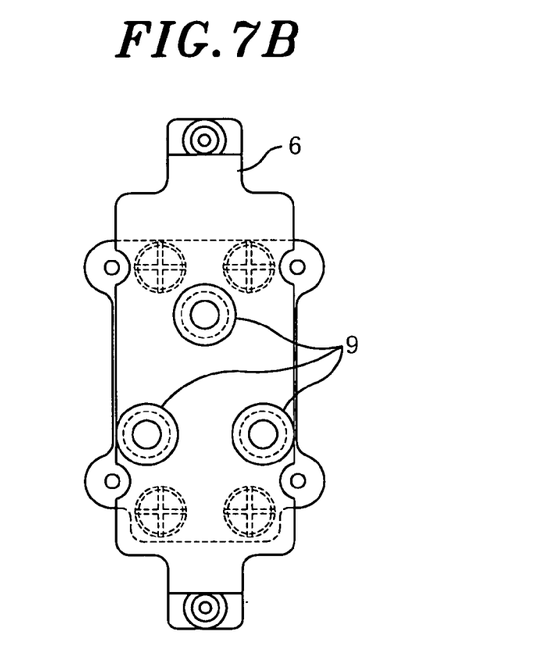

Reference numeral 6 represents a base plate fitted into recess portion 2a of bottom plate 2 for receiving pump unit 5 and is fixed to bottom plate 2 at appropriate positions by using screws. Further, reference 7 is for an attachment plate secured on a bottom surface of pump unit 5 by using screws. The attachment plate 7 is mounted on base plate 6 via first resilient members 8 disposed at four corner portions of base plate 6 and second resilient members 9 installed at positions closer to the center of base plate 6 than first resilient members 8, wherein first resilient members 8 are formed of, e.g., coil springs and second resilient members are of columnar shape and formed of elastic material such as rubber.

Here, each second resilient member 9 includes engagement portions 9a formed along the circumference of an upper and a lower end thereof, wherein the engagement portions 9a are coupled to edges of openings 6a and 6b provided at base plate 6 and attachment plate 7, respectively. As a result of this coupling, base plate 6 and attachment plate are connected to each other, forming a vibration-absorbing unit. Further, it is preferred to provide, for example, bosses for preventing first resilient members 8 from being bent at portions of base plate 6 and attachment plate 7 where first resilient members 8 are installed.

Moreover, pump unit 5 is supported at inner case 3 elastically as follows.

Reference numerals 10 and 11 refer to third resilient members for elastically supporting pump unit 5 at left, right and front side thereof. Third resilient members 10 and 11 are formed of compression coil springs, and so forth. One end of each of third resilient members 10 and 11 is connected to support plate 12. By inserting the other ends of third resilient members 10 and 11 through respective openings provided at a left, a right and a front portion of inner case 3 to thereby bring them into a pressure-contact with side portions and a front portion of pump unit 5 and then by slide-coupling support plates 12 to coupling portions 14 around the openings, third resilient members 10 and 11 can be post-mounted to inner case 3.

Figure 8:
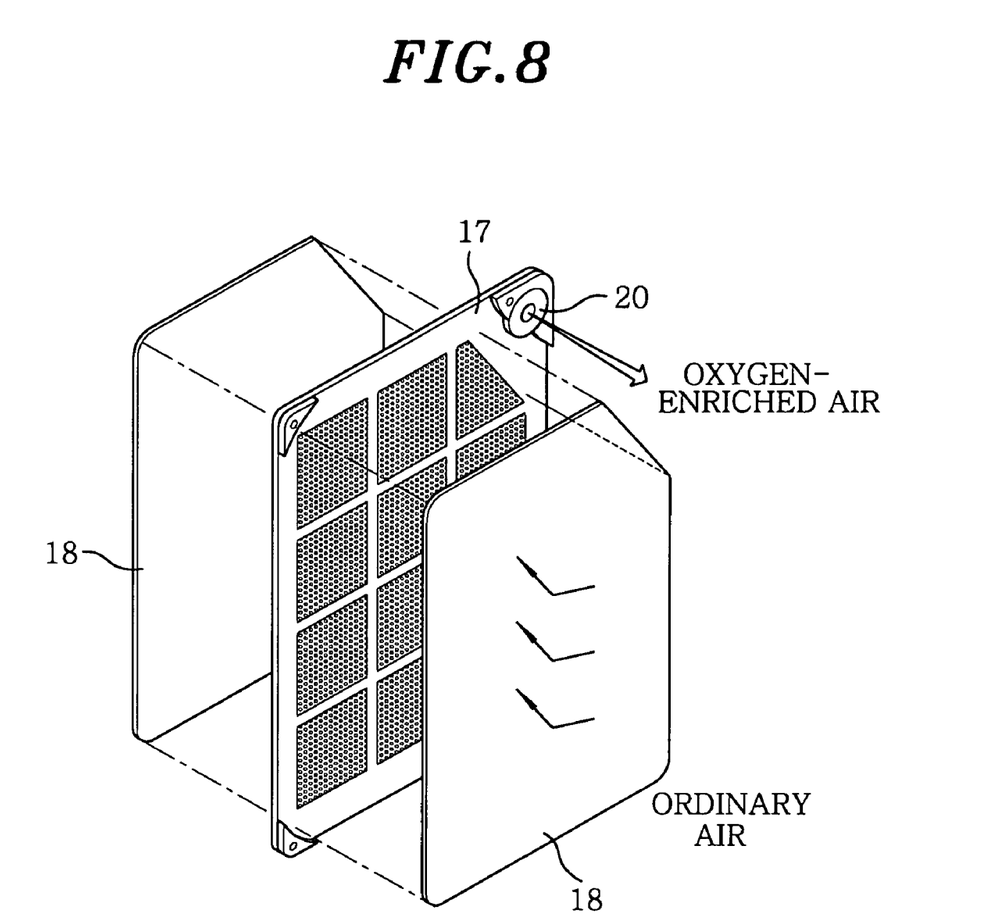
FIG. 8 provides an exploded view of a module of an oxygen enriching unit.
Figure 9A:
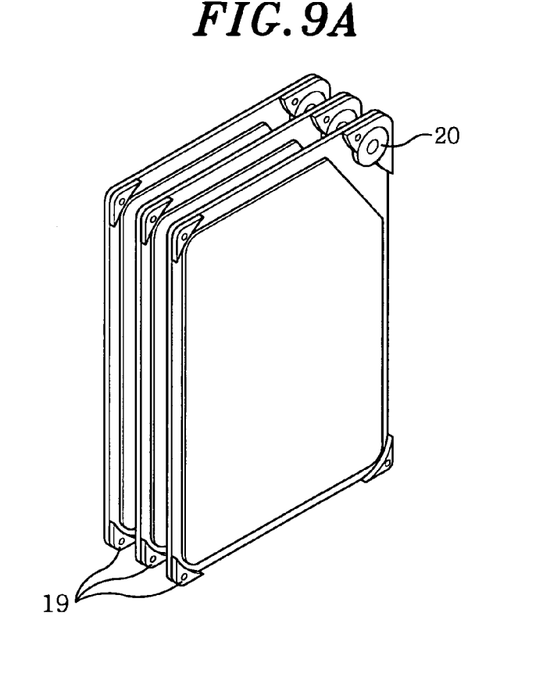
FIG. 9A presents a perspective view showing an assembled state of the module and FIG. 9B sets forth a perspective view of the oxygen enriching unit.
Figure 9B:
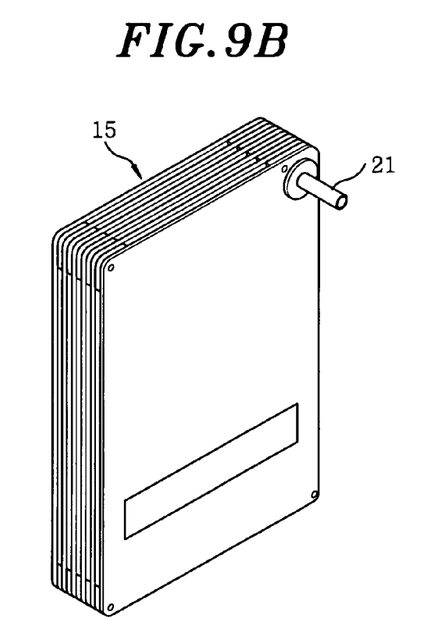

Reference numeral 15 represents an oxygen enriching unit disposed above pump unit 5. Oxygen enriching unit 15 is sandwiched to be fixed by cases 3a and 3b of inner case 3 via packings (not shown) vertically provided on side surfaces thereof. As shown in FIGS. 8 and 9, oxygen enriching unit 15 is of an approximately rectangular parallelepiped unit structure formed by stacking a plurality of modules 19, each of which is provided with mesh frame 17 and substantially rectangular-shaped oxygen enriching membranes 18 attached to two opposite sides of mesh frame 17. Thus, there is formed an air passage between two oxygen enriching membranes 18 in each module 19. By suctioning the inside of the air passage of frame 17, some of the air flowing around oxygen enriching membranes 18 is forced to enter the passage of frame 17 through oxygen enriching membranes 18, so that oxygen-enriched air can be provided. Thus provided oxygen-enriched air is suctioned by pump unit 5 via pipe 21 from sole outlet port 20 of each module 19.

Oxygen enriching membrane 18 includes a flat membrane of organic polymer. Since oxygen enriching membrane 18 has oxygen permeability higher than nitrogen permeability, air of a high oxygen concentration, i.e., oxygen-enriched air, can be obtained. Oxygen content in the atmosphere is about 21%. However, by the suctioning of pump unit 5, the oxygen-enriched air containing about 30% of oxygen therein can be obtained.

Reference numeral 22 is for a discharge port opened at top plate 4 of main body 1. Discharge port 22 is connected to a discharging side of pump unit 5 via pipe 23 to discharge the oxygen-enriched air outputted from pump unit 5 out of main body 1. Reference numeral 23a is for a muffler installed on pipe 23. Muffler 23a enlarges a cross sectional area of air passageway to reduce a noise.

Reference numeral 24 is for a ventilating unit disposed behind pump unit 5. Ventilating unit 24 serves to suction exterior air into oxygen enriching unit 15 inside inner case 3 through air inlet opening 25, which is provided at a rear side of main body 1 to face oxygen enriching unit 15. Then, ventilating unit 24 directs the flow direction of the introduced air downward, to thereby allow the air to be discharged via air outlet opening 26 after cooling pump unit 5. Besides the function of cooling pump unit 5, ventilating unit 24 also has an effect of preventing a decrease in oxygen enriching efficiency by providing fresh exterior air to oxygen enriching unit 15. Furthermore, in accordance with the preferred embodiment, the interior of inner case is utilized as an air passage, and air inlet opening 25 and air outlet opening 26 are provided on a same side of main body 1, i.e., on the rear side thereof in this preferred embodiment.

Reference numerals 29 and 30 are for hollow portions provided in the respective side surfaces of inner case 3 between which oxygen enriching unit 15 is interposed. The formation of hollow portions 29 and 30 is allowed because the width of oxygen enriching unit 15 is narrower than that of pump unit 5 disposed therebelow. Reference numeral 31 is for a control unit including a control board having electronic components 31a mounted thereon, and the like. Control unit 31 is disposed at hollow portion 29 and controls pump unit 5, ventilating unit 24, and so forth. Reference numeral 32 represents a rechargeable secondary battery detachably mounted to hollow portion 30 to serve as a power supply of pump unit 5, ventilating unit 24, control unit 31, and so on. Secondary battery 32 is capable of being recharged via power supply terminal 33 installed at a lower side surface of main body 1 by an external power source such as an AC power source or a cigarette lighter jack (not shown) in a car.

Figure 1A:
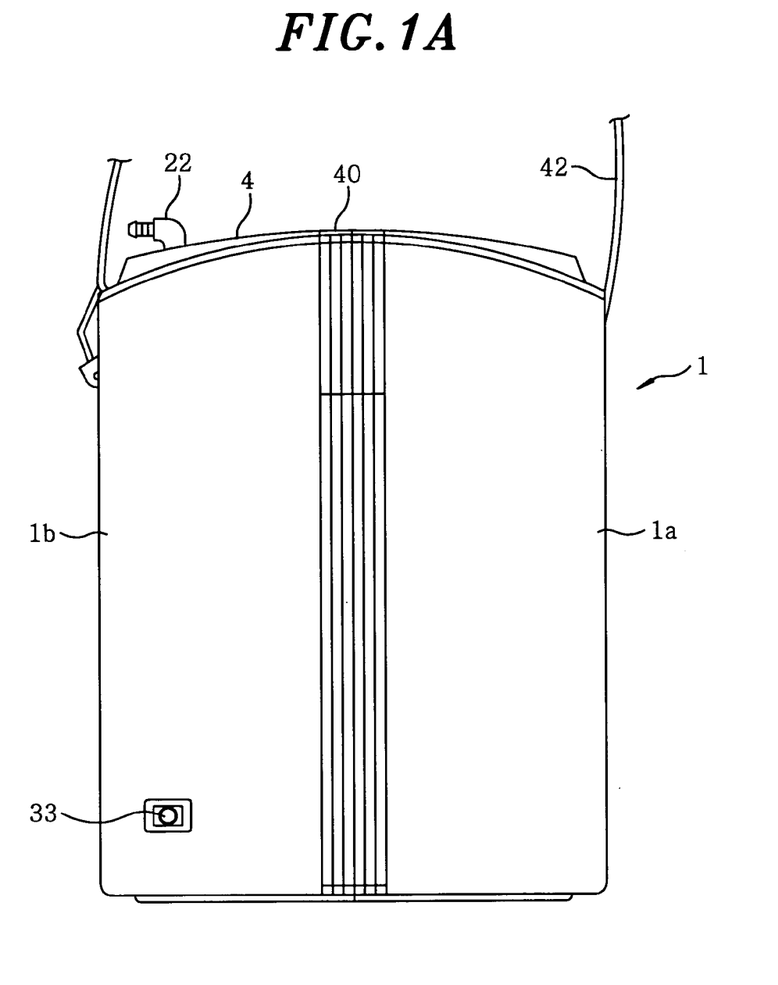
FIG. 1A is a left side view of an oxygen enrichment apparatus in accordance with a preferred embodiment of the present invention and FIG. 1B provides a side view of a power adapter to be connected to the oxygen enrichment apparatus shown in FIG. 1A.
Figure 1B:
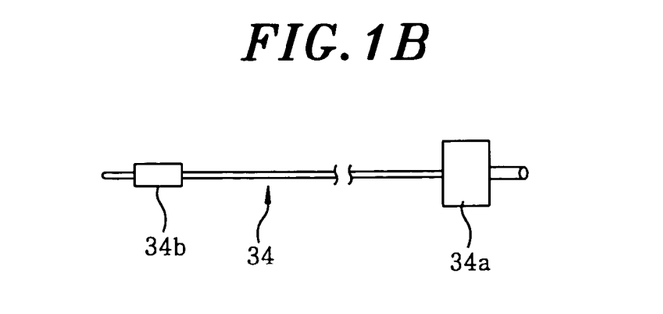
Figure 2:
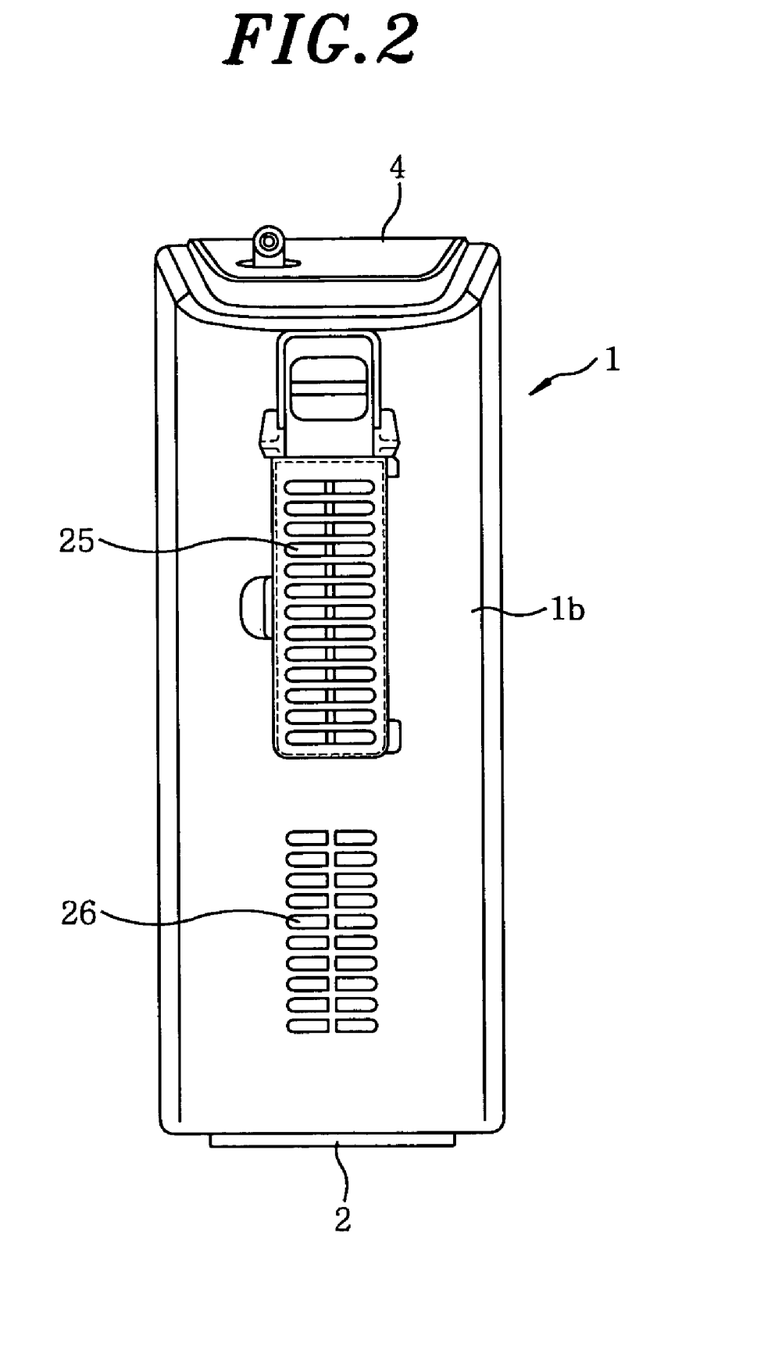
FIG. 2 presents a rear view of the oxygen enrichment apparatus.
Figure 3:
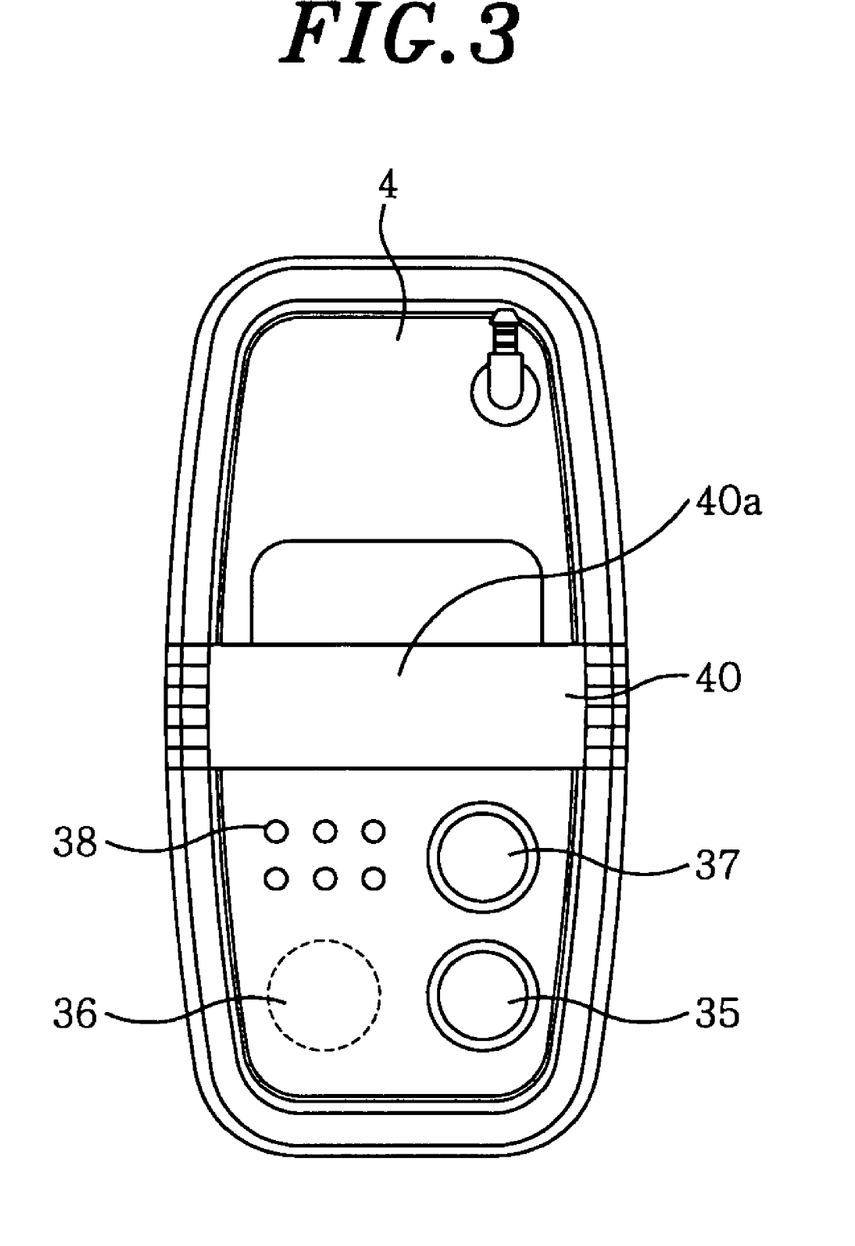
FIG. 3 sets forth a plan view of the oxygen enrichment apparatus.
Figure 4:
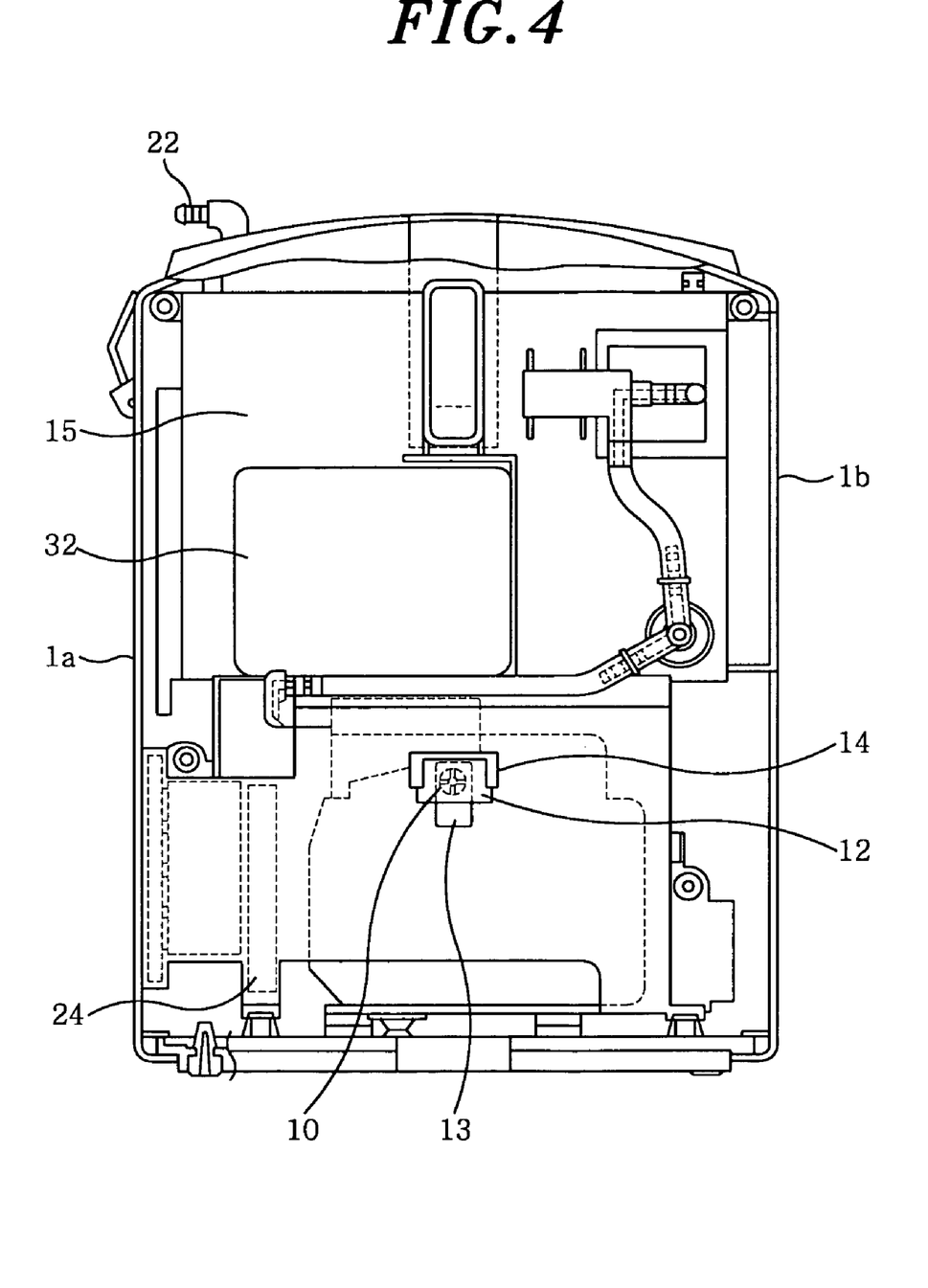
FIG. 4 depicts a left side view of the oxygen enrichment apparatus, wherein a case is removed therefrom.
Figure 5:
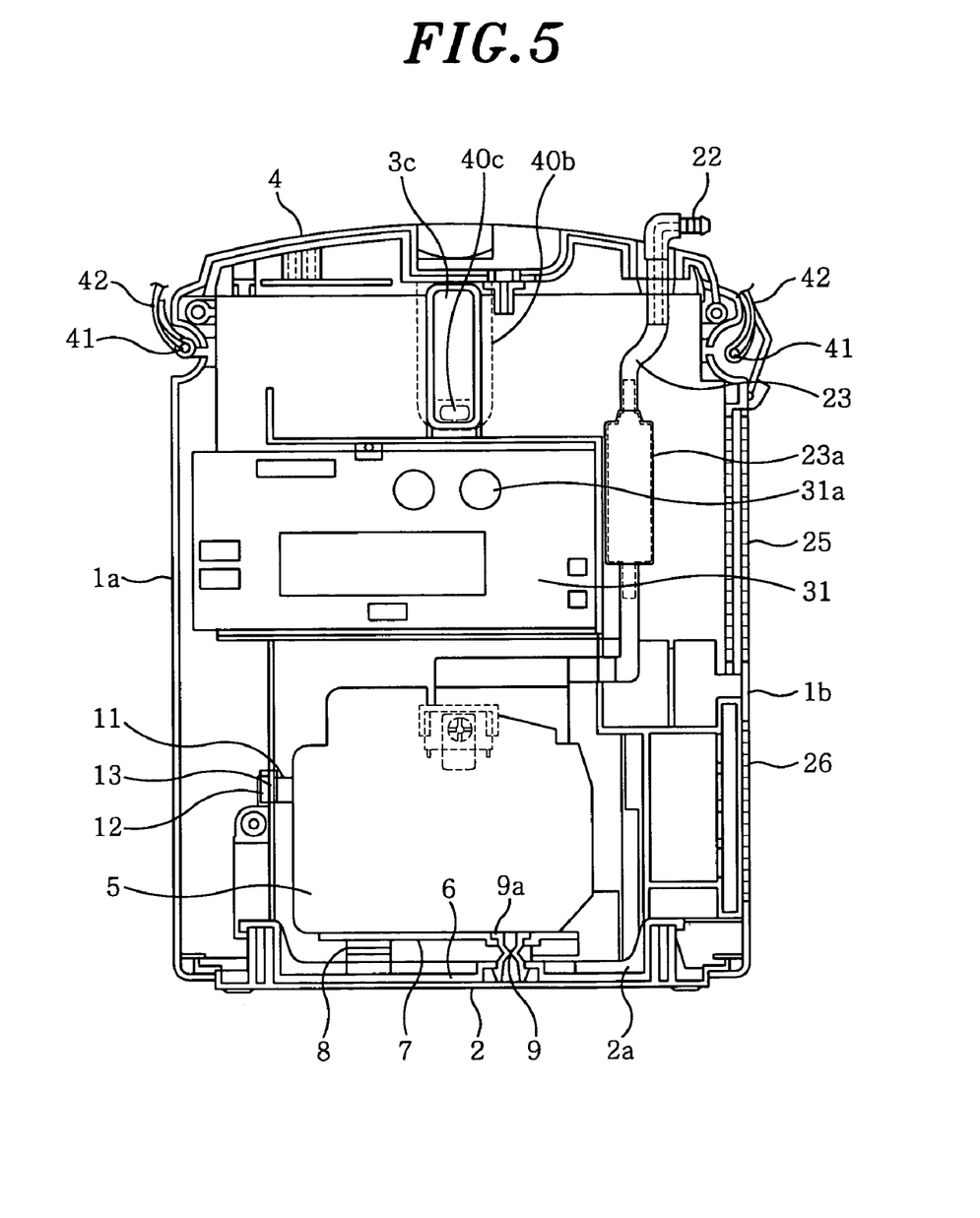
FIG. 5 shows a right side view of the oxygen enrichment apparatus from which the case is removed.

Power supply terminal 33 also serves as a power source terminal in case of using an AC power source. Specifically, by connecting output plug 34b of power adapter 34, which has plug-integrated transformer 34a at one end and output plug 34b at the other end, to power supply terminal 33, the AC power source can be used as a power supply of the oxygen enrichment apparatus. That is, under the control of control unit 31, the AC power source is used as the power supply when plug-integrated transformer 34a is plugged in a plug socket, whereas secondary battery 32 is used as the power supply when plus-integrated transformer 34a is not plugged in. Furthermore, it is also possible to use a battery of a car as the power supply of the oxygen enrichment apparatus by electrically connecting power supply terminal 33 to a cigarette lighter jack in the car.

Reference numeral 35 is for an operation switch provided at top plate 4 of main body 1, and reference numeral 36 represents an operation display unit for displaying an operational state of main body 1. Reference numeral 37 is for a timer switch for setting an operation time. By setting the operation time to be, for example, 30 minutes, 1 hour or 3 hours by using timer switch 37, the operation of oxygen enrichment apparatus can be performed for a predetermined time period. Reference numeral 38 represents a timer display unit for displaying the operation time set by timer switch. Each of the above display units is comprised of an LED, a lamp or the like.

Reference numeral 40 is for a handle for use in carrying main body 1. Grip portion of handle 40 is located flush with the top surface of top plate 4. When viewed from front, handle 40 is of a substantially bottom-side opened rectangular shape or inverted U shape and there are provided shaft portions 40c at two leg portions 40b on both sides of grip portion 40a, respectively. By inserting shaft portions 40c through elongated hole 3c extended in vertical direction at the upper portion of inner case 3, handle 40 is configured to be slidable in the vertical direction and rotatable back and forth about shaft portions 40c.

Reference numeral 41 is for hooks provided at a front and a rear portion of the upper part of main body 1. By connecting a strap to hooks 41, it becomes possible to use main body 1 while hanging it around the shoulder of the user.

Figure 10:
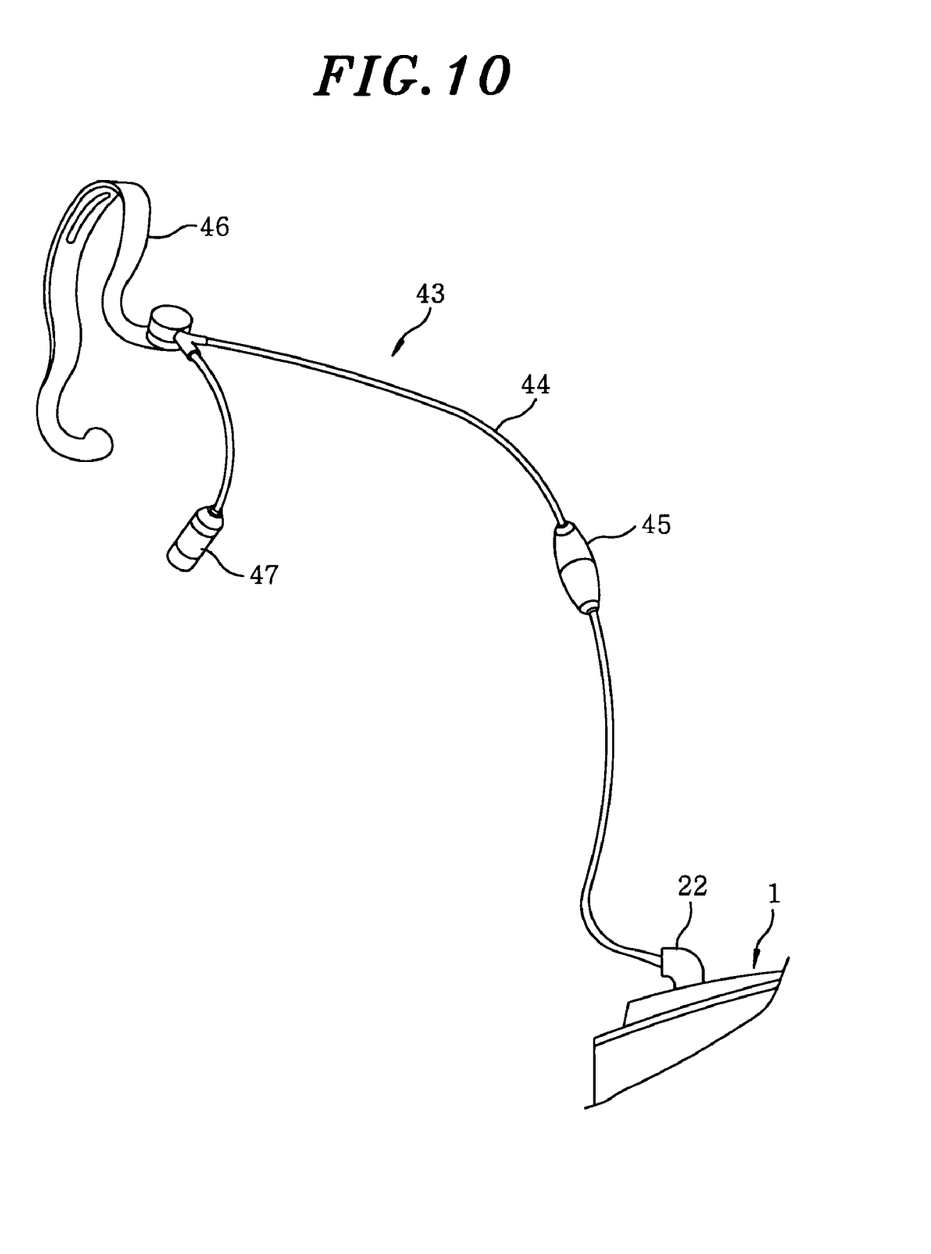
FIG. 10 illustrates a perspective view of an oxygen-enriched air discharge unit of the oxygen enrichment apparatus.

Reference numeral 43 is for an oxygen-enriched air discharge unit which is connected to discharge port 22 opened at top plate 4 of main body 1 when used. Oxygen-enriched air discharge unit 43 includes flexible tube 44 whose one end is connected to discharge port 22 while the other end thereof is coupled to discharge member 46; and condensed water collecting unit 45 installed on tube 44 to gather therein condensed water contained in the oxygen-enriched air. In this preferred embodiment, discharge member 46 is of a headset type and is configured such that its upper part is worn by the user around his/her head, neck or ears, wherein its mouthpiece 47 installed at a lower part thereof is arranged to face the mouth of the user. Therefore, the user can inhale the oxygen-enriched air without using his/her hands.

Hereinafter, the operation of the oxygen enrichment apparatus having the above configuration will be described.

First, the user puts on discharge unit 43 around his/her head, neck or ears. Then, if the user turns on operation switch 35, a power is supplied to pump unit 5 and operation display unit 46 for displaying the power-on-state is turned on. At the same time, pump unit 5 is operated based on the time period set by timer switch 37, and the operation of ventilating unit 24 is also initiated. By the operation of ventilating unit 24, exterior air is suctioned through air inlet opening 25 provided in main body 1, and the exterior air passes through oxygen enriching unit 15 and is then discharged out of main body 1 via air outlet opening 26. Meanwhile, some of the exterior air passing through oxygen enriching unit 15 is introduced inside frame 17 of oxygen enriching unit 15 by the operation of pump unit 5, to be outputted as oxygen-enriched air. The oxygen-enriched air is sent to discharge port 22 and is then discharged through mouthpiece 47 of discharge member 46 of oxygen-enriched air discharge unit 43 via tube 44, to thereby allow the user to inhale the oxygen enriched air through mouth or nose.

Here, main body 1 is typically placed on an installation surface such as the top of a desk or a floor such that bottom plate 2 thereof contacts the installation surface. In case of main body 1 being used in such an arrangement, the vibrations of pump unit 5 serving as a vibration generating source is absorbed by the elasticity of first and second resilient members 8 and 9 without being transferred to main body 1. Accordingly, main body 1 is not vibrated, which allows the user to use the apparatus comfortably.

Further, main body 1 can be used by being laid down horizontally such that left or right case 1a or 1b contacts the installation surface. In such a case, third resilient members 10 and 11 will support pump unit 5 elastically, while absorbing vibrations generated by pump unit 5. As a result, the vibrations can be prevented from being transferred to main body 1 in this case, too. Therefore, even in case main body 1 is laid down horizontally, it is possible to use main body 1 comfortably without suffering from vibrations thereof. Moreover, an external force or an excessively great force can be prevented from being applied to, for example, a joint between pump unit 5 and bottom plate 2 and a joint between pump unit 5 and pipe 23. As a consequence, reliability thereof can be improved.

As described above, the oxygen enrichment apparatus in accordance with the first embodiment of the present invention includes power supply terminal 33 capable of being connected to an external power source; and secondary battery 32. Therefore, it is possible to use the oxygen enrichment apparatus outdoors or inside an automobile by using secondary battery 32 as well as indoors by using an AC power source. That is, if operation switch 35 is turned on under the condition that power adapter 34 is not plugged in a plug socket, power is automatically supplied from secondary battery 32, so that the above-described operations of the apparatus can be performed. Therefore, the user can use the oxygen enrichment apparatus outdoors, for example, while walking or in a car, to inhale the oxygen-enriched air. Furthermore, in case of using the apparatus in the car, power can be obtained or secondary battery 32 can be recharged from a cigarette lighter jack via power supply terminal 33. Therefore, it becomes possible to use the oxygen enrichment apparatus for an extended period of time.

Further, secondary battery 32, which emits heat upon charging or discharging, is disposed at one side of oxygen enriching unit 15 cooled by the exterior air introduced by ventilating unit 24, and control unit 31, which emits heat upon operating, is disposed at the opposite side of oxygen enriching unit 15. Therefore, secondary battery 32 and control unit 31 can be efficiently cooled during operation. As a result, earlier degradation of secondary battery 32 can be prevented and the reliability of control unit 31 can be improved.

Further, by disposing pump unit 5 of relatively great size and mass at a lower portion of main body 1 and light-weighted oxygen enriching unit 15 at an upper portion thereof, stability of main body 1 can be enhanced. Moreover, by installing secondary battery 32 and control unit 31 in dead spaces formed on both sides of oxygen enriching unit 15 which is relatively thin, the overall thickness of main body 1 can be reduced, thereby making it easier to handle, carry or operate main body 1.

In addition, since air inlet opening 25 and air outlet opening 26 are provided on the same side of main body 1, limitation in installation of main body 1 can be reduced compared with a case where they are formed on different sides of main body 1. That is, in case air inlet opening 25 and air outlet opening 26 are provided at different sides of main body 1, main body 1 cannot be installed in a way that any one of the two sides contacts installation surface (because suctioning and evacuation of air cannot be performed due to the closure of air inlet opening 25 and air outlet opening 26 by the installation surface). However, in accordance with the preferred embodiment of the present invention, any one of five sides of main body 1 excepting the one with air inlet opening 25 and air outlet opening 26 can be used as bottom when main body 1 is installed. Therefore, degree of freedom in selecting the way of installing main body 1 can be increased, which in turn improves usability. Further, since main body 1 can be used by placing it vertically or horizontally, limitation in installing main body 1 is reduced, so that the usability can be further increased.

Moreover, the oxygen enrichment apparatus can be carried by drawing out handle 40 and grasping it or by connecting strap 42 to hooks 41, provided at the front and the rear portion of the upper part of main body 1, and hanging strap 42 around the shoulder of the user. In the latter case, particularly, the user can use the oxygen enrichment apparatus while walking or exercising by using, for example, an exercise bicycle. In such cases, since main body 1 rocks, a transverse external force would be applied to pump unit 5. However, the transverse external force is absorbed by third resilient members 10 and 11, so that pump unit 5 is prevented from directly contacting the inner wall of inner case 3, which in turn prevents vibrations of main body 1 that might be regarded as a problem by the user. As a result, the user can use the oxygen enrichment apparatus comfortably.

As described above, in addition to a typical installation of main body 1 where bottom plate 2 contacts an installation surface, main body 1 can be used by being laid down horizontally. Further, even when main body 1 rocks, the user can use it comfortably. Therefore, limitation in the way of using main body 1 can be reduced, resulting in improvement of usability while enabling the use of main body 1 in a wider range of places.

Furthermore, since handle 40 is configured to be extensible/contractible, it can be accommodated in main body 1 after being used, thereby providing a good appearance without occupying a space when it is not in use. Accordingly, it becomes possible to provide an oxygen enrichment apparatus of a high usability.

Figure 11:
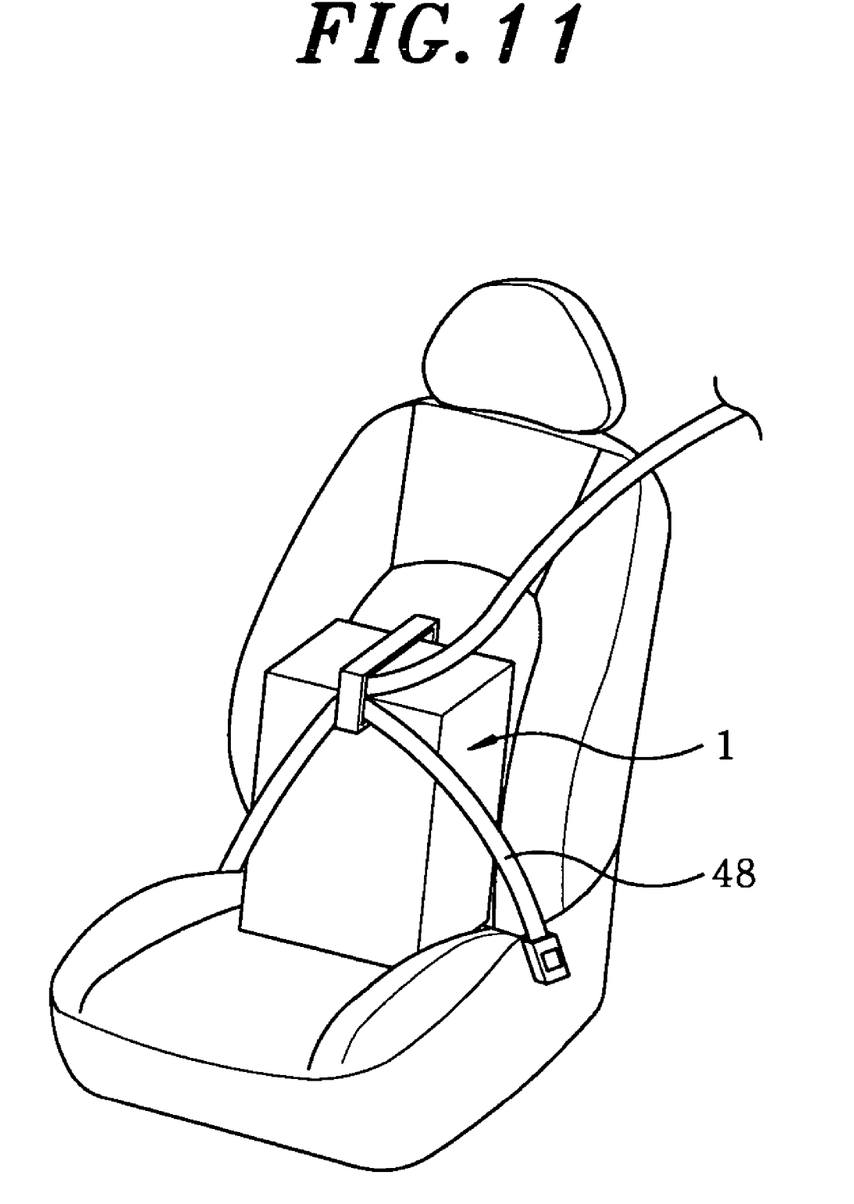
FIG. 11 shows a perspective view of the oxygen enrichment apparatus fastened to a seat.

In case of using main body 1 inside a car, by drawing out handle 40 and passing seat belt 48 through a space between handle 40 and main body 1, as shown in FIG. 11, main body 1 can be fastened to a seat next to a driver or a rear seat. Accordingly, main body 1 can be prevented from moving in an unexpected direction or falling down, so that the user can use the oxygen enrichment apparatus comfortably. In addition, it also prevents a breakage that might be caused by falling down of main body 1 on the bottom of the car or colliding with a door of the car.

Further, it is possible to unitize components by incorporating pump unit 5 and oxygen enriching unit 15 inside inner case 3. Moreover, by assembling them in a single unit component in advance and allowing it to be mounted to main body 1 later, the assembly can be carried out with ease. Furthermore, since inner case 3 also serves as an air passageway through which air suctioned by ventilating unit 24 flows, there is no need for a separate component serving as the air passageway, thereby reducing costs for the manufacture of the oxygen enrichment apparatus.

Figure 6:
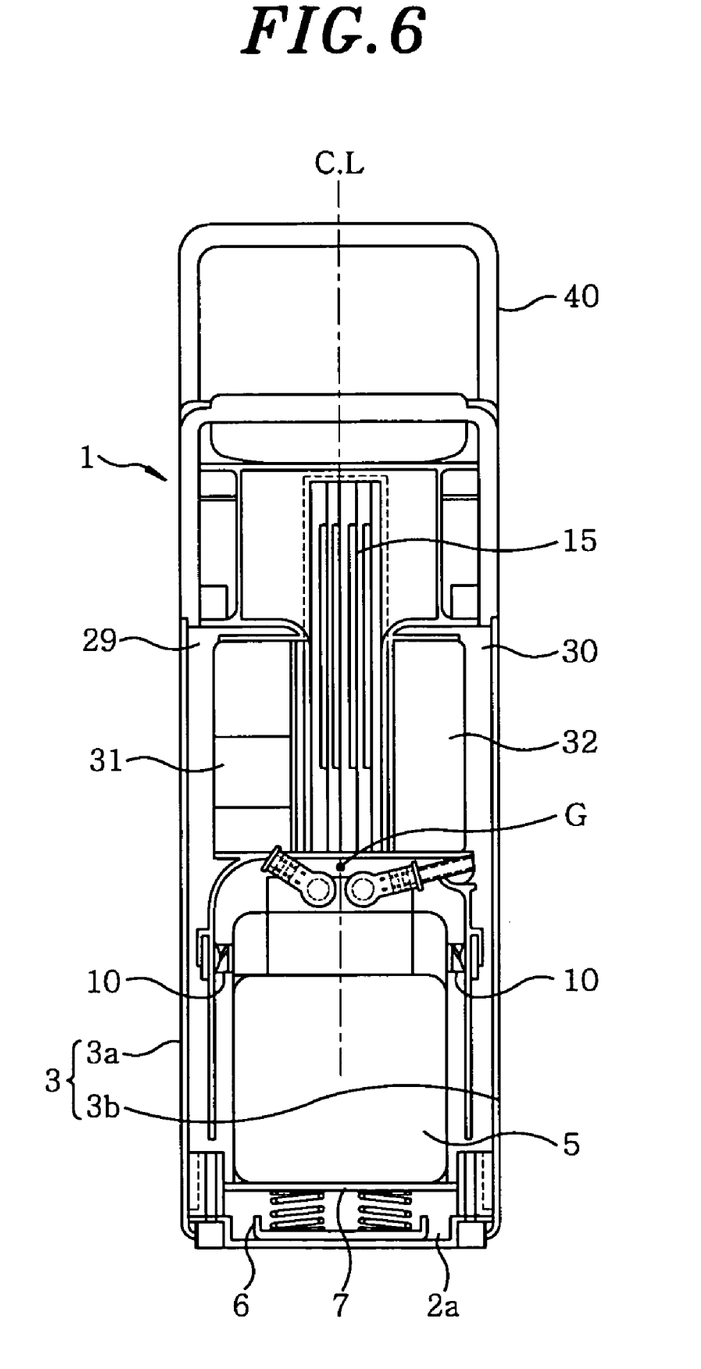
FIG. 6 is a rear view of the oxygen enrichment apparatus from which the case is removed.

As shown in FIG. 6, main body 1 is designed such that its gravity center G lies on central line C.L which passes approximately through an center of handle 40 and extends between control unit 31 and secondary battery 32, it can be prevented that an excessively great force is applied to a user's hand that holds handle 40 while carrying main body 1. Though oxygen enriching unit 15 is located at the center of main body 15 in FIG. 6, since secondary battery 32 is heavier than control unit 31, it is preferable, in general, to slightly move secondary battery 32, oxygen enriching unit 15 and control unit 31 together to the side of control unit 31. In this way, the gravity center G of main body 1 can be located on central line C.L with ease.

Furthermore, though pump unit 5 is configured such that its left, right and front sides are elastically supported by three third resilient members 10 and 11 in this preferred embodiment, it is also possible to support pump unit 5 elastically from four sides thereof including a rear side. In such a case, it is preferable to provide air inlet opening 25 and air outlet opening 26 at top plate 4 which is not used as an installation side in practice. Further, though power adapter 34 including a transformer is employed in this preferred embodiment, it is also possible to incorporate the transformer in main body 1 and connect a common power cord to power supply terminal 33 directly. It is also possible to configure power supply terminal 33 as a charging dedicated terminal and provide an additional power cord or a power supply port for connecting the power cord.

The oxygen enrichment apparatus in accordance with the present invention can be used in any places including outdoors and inside a vehicle such as an automobile or a train where a commercial power source is not available. Thus, the oxygen enrichment apparatus provides highly improved usability with enhanced reliability of components installed therein.

While the invention has been shown and described with respect to the preferred embodiments, it will be understood by those skilled in the art that various changes and modifications may be made without departing from the spirit and scope of the invention as defined in the following claims.

What is claimed is:

1. An oxygen enrichment apparatus comprising:
   a main body including an oxygen enriching unit and a pump unit for supplying oxygen-enriched air obtained by the oxygen enriching unit to a predetermined place, the oxygen enriching unit being disposed above the pump unit;
   a ventilating unit for suctioning exterior air into the main body and discharging the exterior air out of the main body after supplying the exterior air into the oxygen enriching unit;
   a control unit for controlling the pump unit and the ventilating unit;
   a resilient member for elastically supporting a lower portion of the pump unit; and
   an additional resilient member for elastically supporting the pump unit at left, right and front sides thereof;
   wherein the ventilating unit and the control unit are installed in the main body, and the main body further includes therein a secondary battery serving as a power supply for supplying a power to the pump unit, the ventilating unit and the control unit.

2. The apparatus of claim 1, wherein the control unit and the ventilating unit are disposed at opposite sides of the oxygen enriching unit, respectively.

3. The apparatus of claim 1, wherein an inner case incorporating therein the pump unit and the oxygen enriching unit is installed in the main body and the inner case is configured to allow the air suctioned by the ventilating unit to flow therethrough.

4. The apparatus of claim 1, wherein an air inlet opening through which the exterior air is introduced by the ventilating unit and an air outlet opening through which the exterior air is discharged are provided at a same side of the main body.

5. The apparatus of claim 1, wherein a power supply terminal electrically connected to the secondary battery is installed in the main body, the power supply terminal being selectively connected to an external power source.

6. The apparatus of claim 1, wherein hooks for fastening a strap to be hung around a shoulder of a user are installed at appropriate positions at the main body.

7. The apparatus of claim 1, wherein a handle for use in carrying the main body is installed at an upper portion of the main body, and the main body is arranged such that the gravity center thereof lies on a central line that passes substantially through a center of the handle and extends between the control unit and the secondary battery.

8. The apparatus of claim 1, wherein a handle for use in carrying the main body is installed at an upper portion of the main body, and the main body is fastened to a seat of a car by passing a seat belt through a space between the handle and the main body.

9. The apparatus of claim 7, wherein the handle is configured to be extensible/contractible from the main body and slidable in a vertical direction.

10. The apparatus of claim 1, wherein the resilient member includes a first resilient member and a second resilient member, the first resilient member is formed of coil spring, and the second resilient member is formed of elastic material, the second resilient member being of columnar shape.

* * * * *